United States Patent [19]
Lorenz

[11] Patent Number: 5,019,345
[45] Date of Patent: May 28, 1991

[54] METHOD FOR STERILIZING CONTAINERS

[75] Inventor: Jürgen W. Lorenz, Munich, Fed. Rep. of Germany

[73] Assignee: Wagner GmbH, Fed. Rep. of Germany

[21] Appl. No.: 154,345

[22] PCT Filed: May 21, 1987

[86] PCT No.: PCT/EP87/00266
§ 371 Date: Jan. 22, 1988
§ 102(e) Date: Jan. 22, 1988

[87] PCT Pub. No.: WO87/07151
PCT Pub. Date: Dec. 3, 1987

[30] Foreign Application Priority Data
May 22, 1986 [DE] Fed. Rep. of Germany ....... 3617153

[51] Int. Cl.$^5$ .................................................. A61L 2/00
[52] U.S. Cl. ......................................... 422/26; 422/33;
422/300; 220/203; 220/204; 220/366
[58] Field of Search .................. 422/26, 33, 107, 112,
422/113, 295, 296, 297, 300; 220/203, 204, 366,
367, 371, 372; 137/81.1, 81.2, 529

[56] References Cited
U.S. PATENT DOCUMENTS

| 4,228,914 | 10/1980 | Sanderson | 220/203 |
|---|---|---|---|
| 4,251,482 | 2/1981 | Sanderson et al. | 422/26 |
| 4,457,327 | 7/1984 | Pepper | 422/112 |
| 4,512,498 | 4/1985 | Leibinger | 220/366 X |
| 4,551,311 | 11/1985 | Lorenz | 422/26 X |
| 4,748,003 | 5/1988 | Riley | 422/112 |
| 4,770,851 | 9/1988 | Joslyn | 422/26 |
| 4,948,566 | 8/1990 | Gabele et al. | 220/366 X |

Primary Examiner—David L. Lacey
Assistant Examiner—Jeffrey R. Snay
Attorney, Agent, or Firm—Ostrolenk, Faber, Gerb & Soffen

[57] ABSTRACT

In a method for sterilizing a container, a valve body (30) is supported by a gas chamber (24) which is under atmospheric pressure. As a result when a pressure difference is present a static condition arises and keeps the valve open or closed. The valve can be used in a variety of way as influx or admission valve or condensate drain valve or as vacuum or condensate drain valve. The control method effects that in each phase the effective valve is kept open also after reaching the negative or positive peak pressure value until the pressure in the autoclave has adjusted itself to a predetermined closing switching pressure.

6 Claims, 6 Drawing Sheets

METHOD FOR STERILIZING CONTAINERS

Sterilizing containers are used to accommodate clinical sterile material which must be subjected to a steam sterilization. Said sterilization takes place in sterilizers which operate either by the gravitation method (flow method) or in modern equipment increasingly by a vacuum method in which firstly one or more vacuum phases are provided to extract the air from the container, whereafter the container interior is exposed to a steam atmosphere under elevated pressure and elevated temperature, the sterilizing material thereby being subjected to a sterilization. It is advantageous to drain condensate forming so that the material is available as dry as possible after the sterilization. After the steam sterilization time the container is subjected to a further vacuum treatment to withdraw the sterilization steam with any remaining condensate from the container.

To permit the medium exchange the sterilizing containers are either equipped with filters allowing a medium exchange but preventing recontamination or valves are disposed in the container wall which close after the pressure exchange is completed. As influx or vacuum valves check valves according to DE 217,551 or a double valve according to DE 1,217,550 are frequently used. As condensate draining valve bi-metal valves have established themselves which have the advantage over pure check valves that an opening of the valve for draining the condensate can take place throughout the entire sterilizing stage.

A valve which can carry out all these functions is known from U.S. Pat. No. 4,228,914. In this case the gas chamber acting on the valve body is filled with steam during the steam influx phase and at the end of the steam influx phase, i.e. at the start of the sterilization time, the influx opening to the gas chamber is sealed via a shrink hose so that on the subsequent pressure reduction expansion of the gas chamber can effect closure of the valve. This construction requires that after each sterilizing operation the shrink hose must be replaced to ensure the sealing function. The sealing function cannot be effected properly if the shrink hose does not establish a reliable seal. If a leakage flow takes place at the influx opening the seal is jeopardized because the pressure difference necessary for the closure pressure cannot form.

The invention overcomes the problem of providing an operationally safe valve system which operates reliably automatically without addition and setting of parts and can be used in a variety of ways.

Due to the fact that the gas volume remains permanently in the chamber and need not be replenished on each sterilizing operation as in the prior art a reliable and leak-flow-free seal can be achieved in simple manner, and said gas volume can be introduced under a defined pressure at predetermined temperature, in particular under atmospheric pressure, thereby ensuring reliable operation. Conveniently, the differential pressure valve function is subjected to a spring bias, the valve opening or closing operation thereby being displaced somewhat with respect to the atmospheric line. This is however admissible and desirable and the temperature-induced pressure differences within the gas chamber can be compensated adequately as regards the desired function.

The particular difference of the invention compared with conventional check valves resides in that in this case the control force is not the pressure difference acting on the valve disc but a force resulting from the compression or elongation of a pressure pickup (roll diaphragms, diaphragms, concertina hose, corrugated tube, pressure cylinder, barometer cam, etc.) which effects the valve stroke via control rods, control cams, levers, or alternatively (preferably) directly. The decisive part for the opening and closure condition of the valve is therefore played by the pressure present in the sterilizing chamber and not the presence (absence) of a pressure difference at the valve itself. The control force generated by the pressure pickup can be further intensified by supplementing (replacing) part of the gas pressure spring or all of said spring by liquid (preferably water) whose boiling point is set to the desired switching point (usually about 100° C.) This then gives a combination of pressure-dependent and temperature-dependent control.

The valve according to the invention may be used as influx valve for controlling the influx gas jet or as vacuum valve for extracting the steam and finally the valve may also be used as condensate drain valve.

By appropriate valve configuration and arrangement it can be ensured that after the last vacuum phase the container is not completely ventilated again so that the container content is subjected to a vacuum until made available in the operating theater, the penetration of air on opening container showing that said vacuum remained present until said opening.

Other features and advantages of the present invention will become apparent from the following description of preferred embodiments of the invention, with reference to the accompanying drawings.

DETAILED DESCRIPTION OF THE PREFERRED EMBODIMENTS

Figure 1:
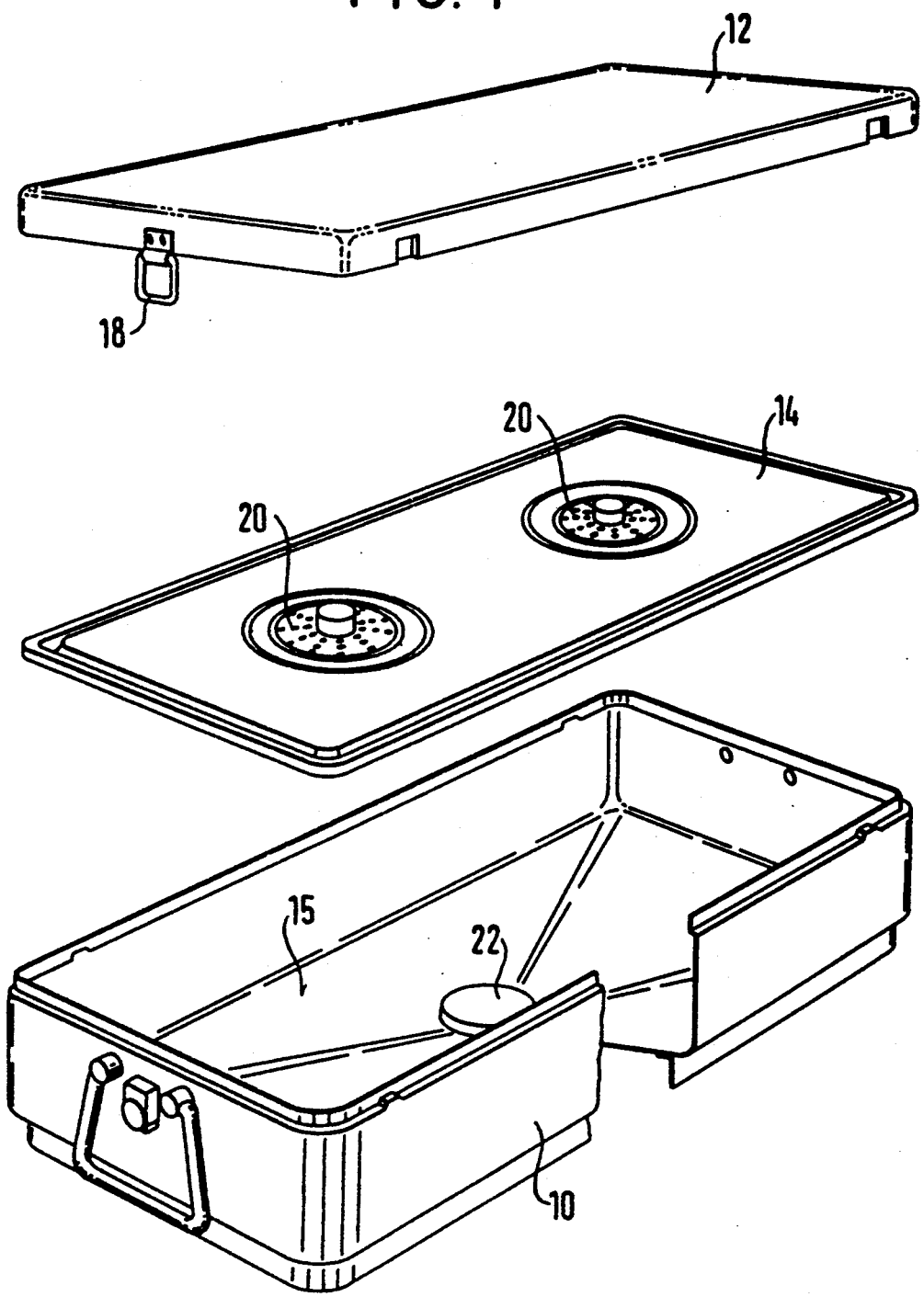
FIG. 1 is an exploded perspective view of a sterilizing container with valves constructed according to the invention.
Figure 2:
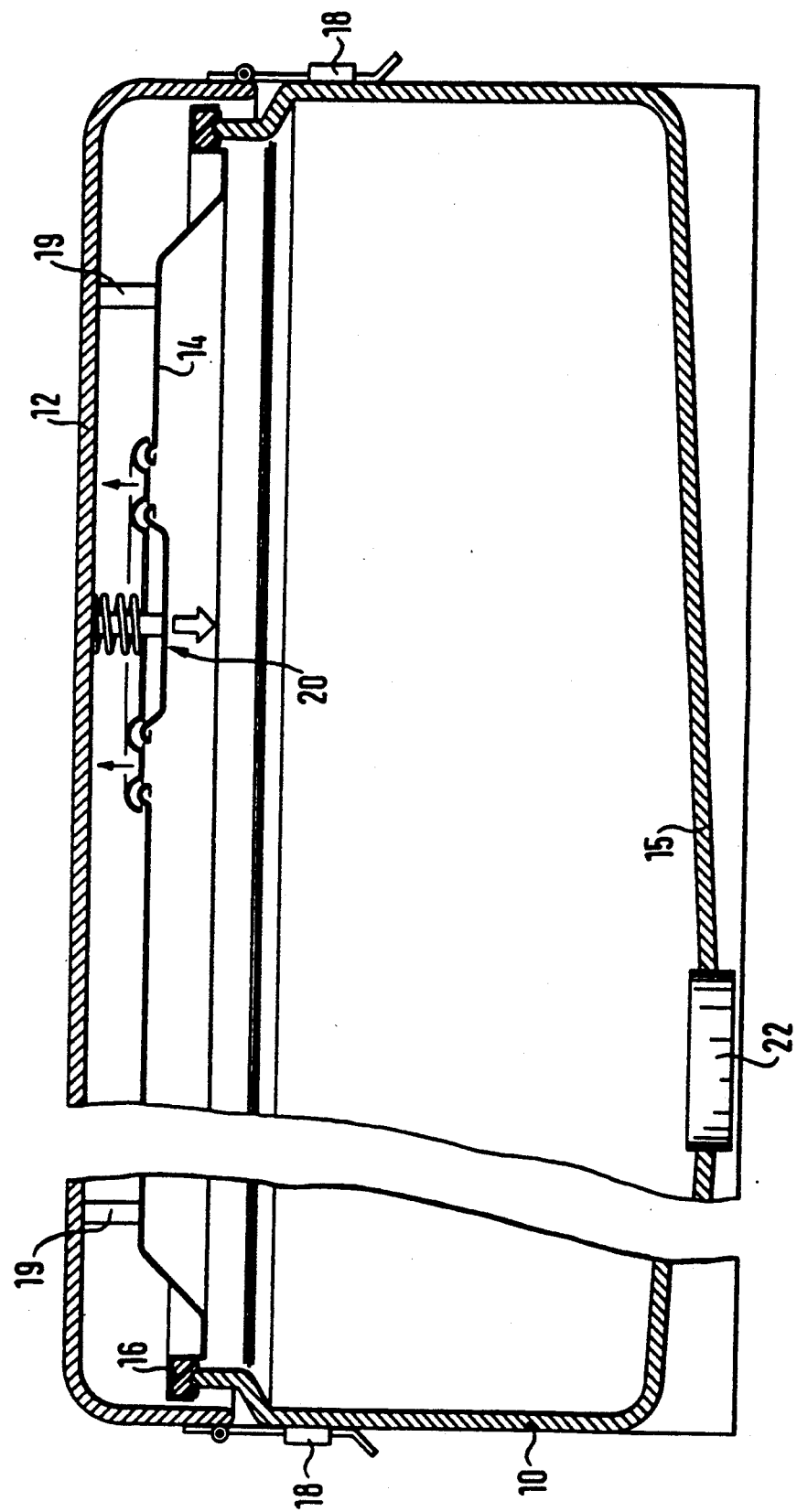
FIG. 2 is a partially broken away longitudinal section of the sterilizing container of FIG. 1.

FIG. 1 shows a sterilizing container of the design described in DE 3,146,349. Said sterilizing container comprises a container lower portion 10, a container cover 12 and an intermediate cover 14 carried by the latter. The intermediate cover 14 is sealed with respect to the upper edge of the container lower portion 10 via a sealing ring 16. The cover 12 is detachably secured to the container lower portion 10 via clamp fasteners 18, the intermediate cover 14 thereby being sealingly biased against the lower portion 10 via the supports 19 carrying the intermediate cover 14. The intermediate cover 14 is equipped with valves 20 which are only indicated schematically in FIGS. 1 and 2. As apparent from FIG. 1 the bottom of the container lower portion 10 drops downwardly from all sides towards the center where a further valve 22 indicated only schematically in FIGS. 1 and 2 is arranged which can serve as condensate drain.

Said valves 20 and 22 form the subject of the invention and are illustrated in various examples of embodiment of the invention in FIGS. 3 to 11. Said valves can be used in sterilizing containers of a great variety of types and their use is not restricted to the embodiment illustrated in FIGS 1 and 2. In particular, the valves 20 may be arranged in a container cover fitted sealingly on the container lower portion or alternatively in the container lower portion.

Common to all the embodiments is a gas chamber 24 which is sealed all round and bordered at least partially by resilient walls and in which a predetermined gas volume under predetermined pressure, preferably dry air under atmospheric pressure, is enclosed. All the valves are rotation-symmetrical with respect to a center axis 26. In all the example (apart from the embodiment of FIG. 4) one of the opposing circular chamber walls 28 carries a valve body in the form of an encircling sealing bead or sealing edge 30 which in the rest state bears on the container wall portion 32 which forms the valve seat. Within the surface portion surrounded by the sealing bead 30 the wall portion 32 is provided with passage holes 34 serving for the exchange of the media.

The chamber wall 28 is stiffened by an inwardly disposed plate 36 of metal or plastic. The opposite chamber wall 38 is likewise stiffened by a plate 40. The cylindrical side wall 42 between the front wall 28 and the rear wall 38 is flexible in such a manner that the spacing between the front and rear wall is variable depending on the pressure differences obtaining. Said beside wall can be made in the manner of a bellows or concertina and the chamber wall can be made in one piece or consist of several parts which are joined sealingly together. The stiffening plates 36 and 40 also serve as spring plates for a biasing helical spring 44 disposed therebetween which pushes the two walls 28, 38 apart and tends to increase the chamber volume. The gas chamber is surrounded by a housing 46 which is provided with openings and which is riveted to the wall portion 32 or otherwise secured. The rear wall 38 can be connected to the housing 46 for example by riveting.

In all the examples the gas pressure of the chamber acts directly on the valve bodies. This has the advantage that the valves can be accommodated compactly on the container wall. If considered expedient in specific cases the gas pressure chamber can also be arranged spaced from the valve bodies and the supporting can be effected via a hydraulic fluid which in turn is supported by the gas spring, for example in a pressure can.

For sterilization of the sterile material received by a sterilizing container in a steam sterilizer the following valve functions are necessary, as already mentioned:

1. Influx valve: Through this valve the steam serving for the sterilization must be introduced into the container interior.

2. Vacuum valve: Through this valve the air originally located in the container and subsequently the steam mixed with the residual air must be extracted from the container.

3. Condensate drain valve: Through this valve the condensate which has formed in the container, for example in the sterilization of (non-porous) instruments, is to be drained.

The various valves similar in their basic function in the examples illustrated can each carry out several functions. However, generally it will be expedient to provide several valves in the cover or in the bottom and to assign to each of said valves only one or at the most two functions. Hereinafter the mode of operation of the individual valves will be described with regard to their preferred use but this does not exclude any use for a different purpose.

Figure 3:
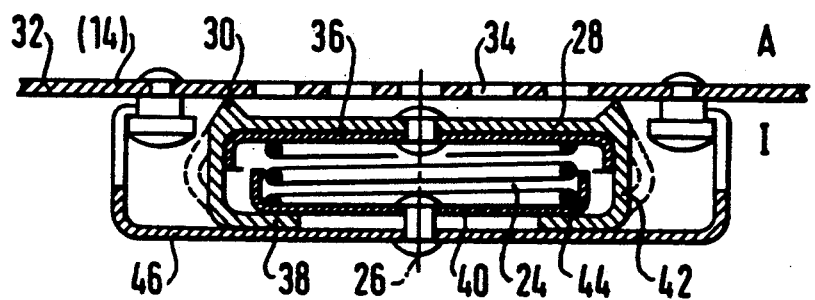
FIG. 3 to FIG. 11 show various examples of valves which can be used in conjunction with a sterilizing container according to FIGS. 1 and 2.

The valve according to FIG. 3 is primarily suitable as influx or admission valve and in this function is conveniently suspended on the wall portion 32 formed as cover or intermediate cover on the inner side of the container.

Before introduction of the sterilizing container into the sterilizer the valve is closed by the bias of the spring 44 and possibly by the bias of the gas pressure chamber 24. The gas pressure chamber is filled with air under atmospheric pressure (i.e., ambient pressure). Fluctuations in the atmospheric pressure do not appreciably affect the operation of the invention. In the initial single or repeated extraction of air or the steam-residual air content in the vacuum phases 1-2-3 (FIG. 12) the valve remains closed because the atmospheric pressure within the chamber 24 is positive with respect to the external pressure and is further increased by heat. In the now following steam admission phase 3-4 the valve is opened, this being done at a point somewhat above atmospheric pressure because of the bias of the spring and possibly because of the pressure increase due to the temperature increase. However, in contrast to conventional check valves the valve according to the invention does not close at the position 4 of maximum pressure but remains open over the entire sterilizing phase 4-5 because the gas chamber remains compressed due to the externally obtaining excess pressure. When the pressure drops between 5 and 6 (FIG. 12) the valve still remains open until at a point somewhat above atmospheric pressure (due to the spring biasing and heating of the air within the chamber) the valve again closes. In the subsequent vacuum phase 6-7-8-9 the valve remains closed.

Figure 4:
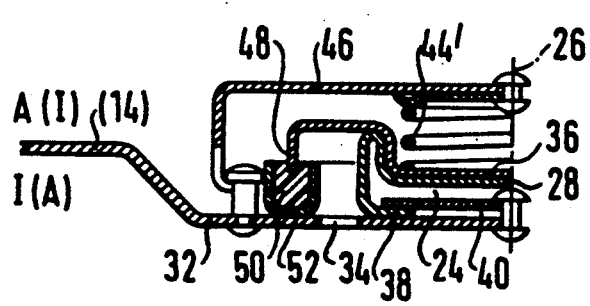

FIG. 4 shows a valve according to the invention in a typical construction and use as vacuum valve. In this case the chamber wall 38 together with the stiffening plate 40 is secured to the one part of the container portion 32 forming the container cover. The stiffening plate 36 bearing in this case externally on the opposite chamber wall 28 extends with an annular edge 48 outwardly and bears on a sealing ring 50 which is inserted into a U-profile 52 fixed on the container cover. The biasing spring 44' bears on the plate 36 and on the valve housing 46.

In all the FIGS. the letter I denotes the container interior and the letter A the space disposed outside the sterilizing container (in the autoclave) (this applies to the preferred use described; a reversal is conceivable for modified construction or modified use).

In the rest state the valve according to FIG. 4 is closed by the bias of the spring 44'. After compensation of the spring bias the valve 4 opens in the vacuum phase just below the atmospheric line and remains open during the entire vacuum phase 1-2-3, the setting preferably being such that the open position is also retained when the internal and external pressures in the vacuum region are equal. During the excess pressure phase 3-4-5-6, in which the sterilization takes place, the valve remains closed due to the externally obtaining excess pressure and opens again in the vacuum phase 6-7-8-9.

Figure 5:
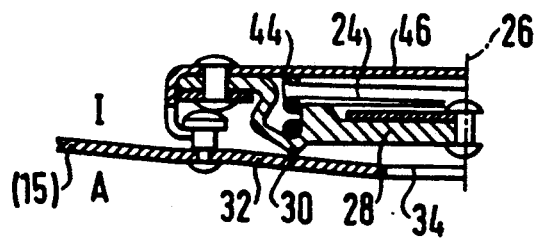

FIG. 5 shows the invention applied to a typical condensate drain valve. In this case the valve is fixed to the inner side of the wall portion 32 formed by the container bottom 15. The condensate drain valve according to FIG. 5 remains in the open position as long as the pressure outside of the chamber 24 is higher than the starting pressure within the chamber, i.e. during the entire sterilizing phase 3-4-5-6 and not only during the influx or admission phase 2-3-4 as is the case with an excess pressure or pressure-limiting check valve. Compared with a bi-metal drain valve the advantage is achieved that the valve according to the invention operates independently of the temperature conditions and has a large stroke and higher application pressure.

Figure 6:
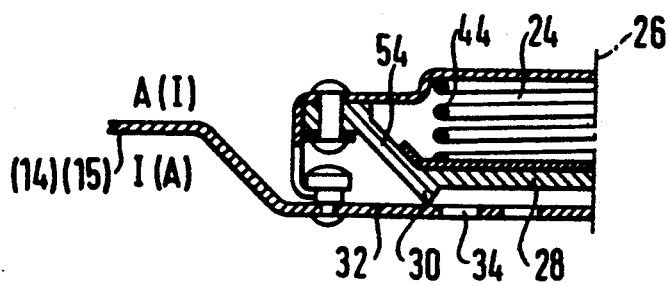
Figure 7:
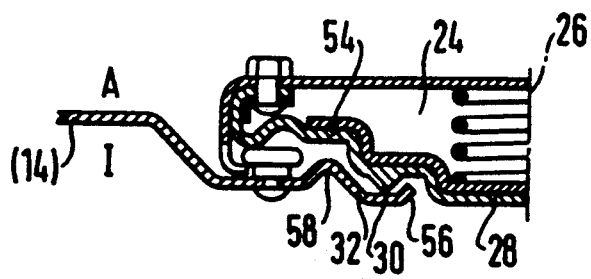
Figure 8:
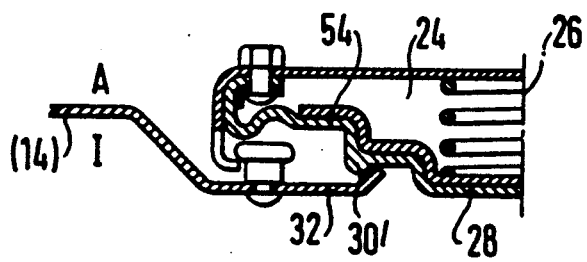

The design according to FIG. 6 permits use as influx valve and in this case the valve is mounted externally on the cover 14. To ensure opening when the outer pressure rises a radially outwardly projecting pressure face 54 is provided with which the outer pressure raises the valve body 30 and when a sealing gap has been formed the outer pressure can engage the entire wall face 28. Otherwise the function is as described in conjunction with FIG. 3.

If the valve according to FIG. 6 is to be used as condensate drain it is inserted into the container bottom 15 in the manner described and then operates in the same manner as the valve described in conjunction with FIG. 5.

FIGS. 7 to 11 illustrate some further modified examples valves according to the invention which operate in the arrangement illustrated as steam admission valve. However, on corresponding modification use as condensate drain valve is also conceivable.

The valve 7 has the particular feature that the container wall 32 is provided with an inwardly projecting edge 56 which surrounds the valve body rib 30. The outwardly lying pressure face 54 which effects the initial raising is not beveled as in the example of embodiment of FIG. 6 but made stepped. The container wall is also provided radially outside the valve body 30 with an inwardly drawn rib 58. In the embodiment according to FIG. 8 said latter portion is made planar and a bean 30' is provided instead of the valve body rib.

Figure 9:
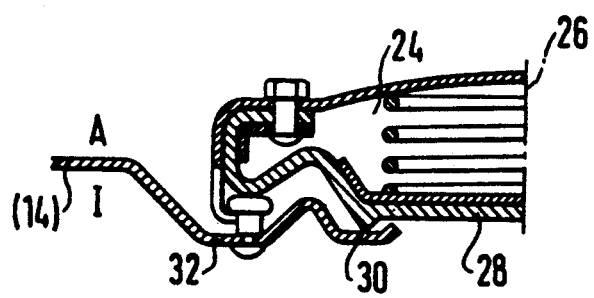

In addition, in the examples according to FIGS. 5 and 9 the valve housing wall forms at the same time the outer boundary of the gas chamber 24.

Figure 10:
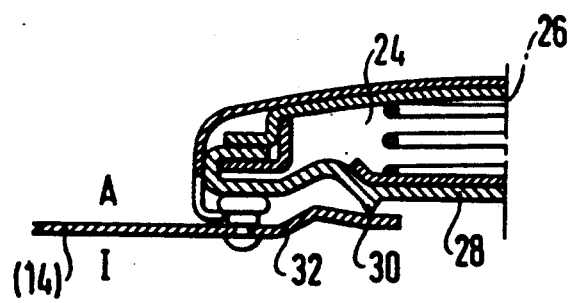
Figure 11:
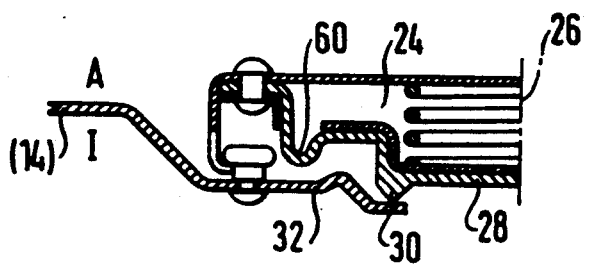

The embodiment of FIG. 10 differs from the remaining examples in the arrangement and configuration of the encircling annular wall. In the embodiment of FIG. 11 the chamber wall extends outside the valve body rib 30 in the plane of the cover and perpendicularly thereto, a resilient bead 60 being formed therebetween.

Figure 12:
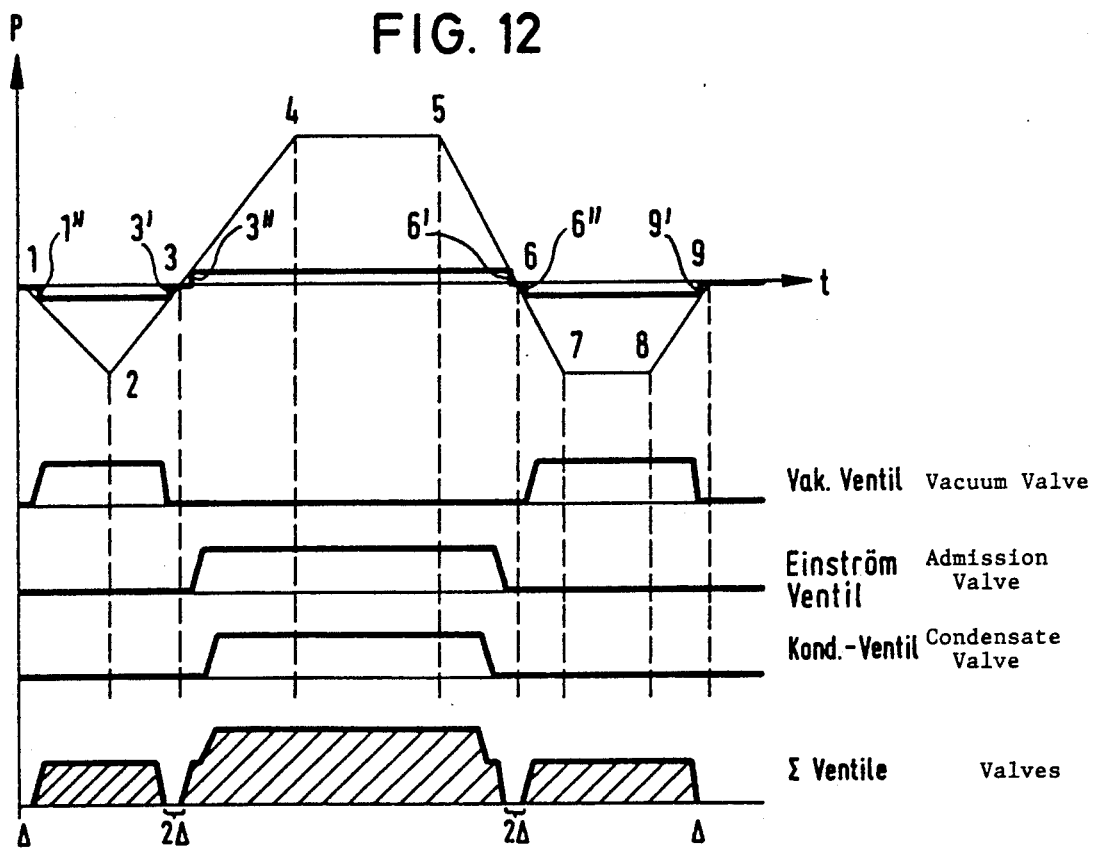
FIG. 12 is a diagram showing a possible time-dependent pressure variation during a sterilizing cycle together with the valve function of the individual valves.

FIG. 12 shows the time-dependent pressure variation P within the sterilizing container and the valve functions. The step-like form of the curves in the region of the zero passage is due to the valve biasing, i.e. by the spring pressure and possibly by the gas pressure within the gas pressure chamber.

The sterilizing operation includes the following phases: single or multiple vacuum phase (1 to 3), to excess pressure phase (3 to 6) with sterilizing phase (4 to 5), after-vacuum phase (5 to 8) ventilation phase (8 to 9). In contrast to known devices the valve effective in each phase is also kept open after reaching the negative or positive peak pressure value until the pressure in the autoclave has adjusted itself to a predetermined closure switching pressure (3', 6', 9'). In addition, the valve effective in each phase is kept closed until the pressure in the autoclave has adjusted itself to a predetermined opening switching pressure (1", 3", 6"). The absolute values of the opening switching pressure and closing switching pressure are conveniently made of equal magnitude.

According to the examples illustrated the valves are controlled in dependence upon the pressure obtaining in the autoclave.

Alternatively or additionally the valve control can also take place in time dependence on the pressure zero passages (atmospheric pressures) in the autoclave or in dependence upon the temperature obtaining in the autoclave. A sensor initiating the switching function may be associated with each valve arrangement. Finally, it is also possible to control the valve arrangement externally.

Figure 13:
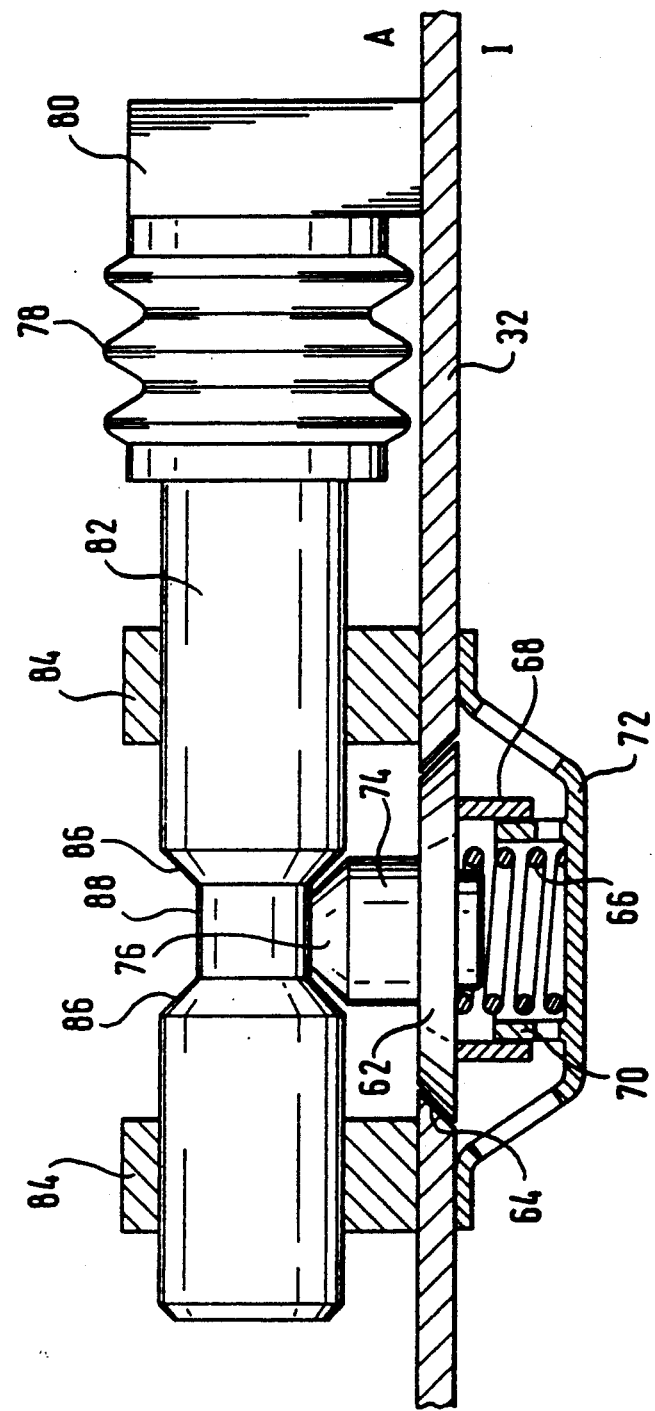
FIG. 13 is a schematic view of a double valve constructed according to the invention.

FIG. 13 shows a double valve which can be used as admission or influx valve or as vacuum valve and furthermore also as condensate drain valve. The valve body 82 cooperating with a valve seat 64 of the container wall portion 32 is biased by a spring 66 into the closure position. The valve body 62 is guided with a cylindrical extension 68 on a bush 70 which is carried via a holder 72 by the container wall 32. The valve body 62 carries an actuating member 74 which has a frustoconical head 76. The gas chamber is surrounded by a bellows 78 which is hermetically sealed and connected at one end to a container-fixed block 80. The other end of the bellows 78 is secured to a thrust rod 82 which is axially displaceably guided in bearing blocks 84. In the region of the actuating member 74 the thrust rod 82 comprises a turned-down portion which is defined by two conical faces 86 and an intermediate cylindrical portion 88.

FIG. 13 shows a center position in which the valve is closed. If the outer pressure increases the bellows 78 is compressed and the thrust rod 82 displaced to the right according to FIG. 13. As a result the valve is opened via the conical slide faces 86 and 76.

If however starting from the center position according to FIG. 13 the pressure drops then the bellows 78 expand and the thrust rod 82 is displaced to the left so that the valve also opens.

The axial length of the cylindrical portion 88 is somewhat greater than the diameter of the head end 76 so that a certain idle movement is incorporated and as a result the valve remains closed within a predetermined pressure difference range.

Accordingly, the valve illustrated in FIG. 13 can perform all the valve functions because it is controlled by the bellows 78 both in the vacuum region and in the excess pressure region.

In all the examples the gas chamber may be set to the particular atmospheric pressure. For this purpose a vent or ventilation valve not shown in the drawings may be provided and permits pressure equalization. However, generally outer weather-induced air pressure fluctuations need not be taken into account and it suffices to provide a pressure equalization to the corresponding altitude where the container is to be used. For this purpose an opening can be provided which can be permanently sealed by a resilient stopper.

In the embodiment illustrated in FIG. 13 the actuating means 78, 82, 86, 88 is secured to the container wall via the bearing blocks 80, 84. However, the invention also covers the case of separating said actuating means from the valve and arranging said means detachably so that the actuating means is connected to the valve only in the sterilizer and the sterilizing container (outside the sterilizer) can be transported and stored without said actuating.

Although the present invention has been described in connection with particular embodiments thereof, many other variations and modifications and other uses will become apparent to those skilled in the art. It is preferred, therefore, that the present invention be limited not by the specific disclosure herein, but only by the appended claims.

In the claims:

1. The method of sterilizing material within an autoclave, comprising the steps of:

locating the material within a container, the container including a vacuum valve and an admission valve;

locating the container within the autoclave;

thereafter reducing the pressure within the autoclave from a starting pressure to a first negative peak pressure and thereafter increasing the pressure within the autoclave from the first negative peak pressure to the starting pressure;

opening the vacuum valve while reducing the pressure within the autoclave from said starting pressure to said first negative peak pressure, keeping the vacuum valve open while the pressure within the autoclave is at the first negative peak pressure and closing the vacuum valve while increasing the pressure within the autoclave from said first negative peak pressure to said starting pressure;

thereafter increasing the pressure within the autoclave from the starting pressure to a positive peak pressure and thereafter reducing the pressure within the autoclave from the positive peak pressure to the starting pressure;

opening the admission valve while increasing the pressure within the autoclave from the starting pressure to the positive peak pressure, keeping the admission valve open while the pressure within the autoclave is at the positive peak pressure and closing the admission valve while reducing the pressure within the autoclave from the positive peak pressure to the starting pressure;

thereafter reducing the pressure within the autoclave from the starting pressure to a second negative peak pressure and thereafter increasing the pressure within the autoclave from the second negative peak pressure to an end pressure; and opening the vacuum valve while reducing the pressure within the autoclave from the starting pressure to the second negative peak pressure, keeping the vacuum valve open while the pressure within the autoclave is at the second negative peak pressure and closing the vacuum while increasing the pressure from the second negative peak pressure to the end pressure.

wherein the vacuum valve includes a sealed chamber which expands and contracts according to the pressure within the autoclave, wherein reducing the pressure within the autoclave from the starting pressure to either the first or second negative peak pressure causes the chamber to expand and thereby open the vacuum valve, wherein maintaining the pressure within the autoclave at either the first or second negative peak pressure keeps the chamber expanded and thereby keeps the vacuum valve open and wherein increasing the pressure within the autoclave either from the first negative peak pressure to the starting pressure or from the second negative peak pressure to the end pressure causes the chamber to contract and thereby close the vacuum valve.

2. The method of claim 1, further comprising the step of maintaining the pressure within the autoclave at the positive peak pressure for a predetermined period of time.

3. The method of claim 1, wherein the admission valve includes a sealed chamber, wherein the step of increasing the pressure within the autoclave from the starting pressure to the positive peak pressure causes the admission valve chamber to contract and thereby open the admission valve, wherein a step of maintaining the pressure within the autoclave at the positive peak pressure keeps the admission valve chamber contracted and thereby keeps the admission valve open and wherein the step of reducing the pressure within the autoclave from the positive peak pressure to the starting pressure causes the admission valve chamber to expand and thereby close the admission valve.

4. The method of claim 1, wherein the vacuum and admission valves are defined by a single valve means.

5. The method of claim 1, wherein the container further includes a condensate valve, the method including the steps of opening the condensate valve while increasing the pressure within the autoclave from the starting pressure to the positive peak pressure, keeping the condensate valve open while the pressure within the autoclave is at the positive peak pressure and closing the condensate valve while reducing the pressure within the autoclave from the positive peak pressure to the starting pressure.

6. The method of claim 5, wherein the step of opening the admission valve precedes the step of opening the condensate valve and the step of closing the condensate valve precedes the step of closing the admission valve.

* * * * *